United States Patent [19]

Ender

[11] Patent Number: 4,475,545
[45] Date of Patent: Oct. 9, 1984

[54] BONE-NAIL

[76] Inventor: Hans G. Ender, Ferstelgasse 6/20, A-1090 Vienna, Austria

[21] Appl. No.: 447,243

[22] Filed: Dec. 6, 1982

[51] Int. Cl.³ .......................... A61F 5/04; A61B 17/18
[52] U.S. Cl. ................................ 128/92 BC; 128/92 G
[58] Field of Search ............ 128/92 BC, 92 B, 92 BA, 128/92 BB, 92 R, 92 G

[56] References Cited

U.S. PATENT DOCUMENTS

| | | | |
|---|---|---|---|
| 2,998,007 | 8/1961 | Herzog | 128/92 BC |
| 3,334,624 | 8/1967 | Schneider et al. | 128/92 R |
| 3,441,017 | 4/1969 | Kaessmann | 128/92 BC |

FOREIGN PATENT DOCUMENTS

| | | | |
|---|---|---|---|
| 2246274 | 3/1974 | Fed. Rep. of Germany | 128/92 BC |
| 2292459 | 6/1976 | France | 128/92 G |

Primary Examiner—Ronald L. Frinks
Attorney, Agent, or Firm—Holman & Stern

[57] ABSTRACT

A bone-nail for long hollow bones consists of a tubular base member being distally provided with a tip and proximally comprising a head for applying a driving instrument. The distal edge portion of the base member has a closed cross section and is conveniently provided with two pairs of holes, both holes of one pair of holes being coaxially arranged on a common axis passing through the nail in transverse relation to its longitudinal direction and both axes of the said both pairs of holes being located in different planes extending in transverse direction relative to the longitudinal direction of the nail and intersecting one another with an acute angle preferably having a value between 10° and 60°. The middle portion adjoining the distal edge portion is slotted in longitudinal direction of the nail, the slot being widened by forcibly bending its edges so that this middle portion has a cross section being greater than the closed cross section of the distal edge portion. The proximal edge portion adjoining the middle portion again has a closed cross section corresponding to the cross section of the distal edge portion and is provided with two pairs of holes, the axes of these pairs of holes being located in a common plane extending substantially in normal direction to the plane including the curved nail axis and extending within the area of the said pairs of holes in direction of the nail axis, said axes intersecting one another within the interior of the nail and preferably intersecting one another with an approximately right angle. The holes within the proximal edge portion are conveniently provided with a thread.

7 Claims, 5 Drawing Figures

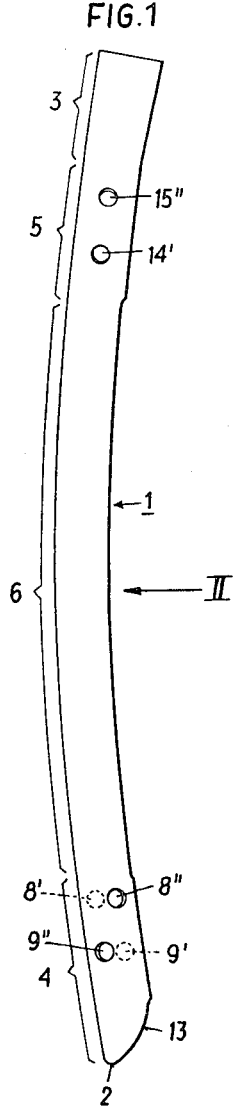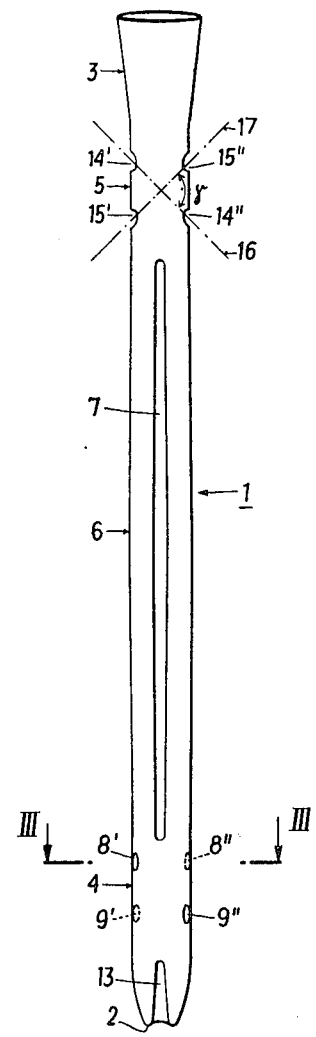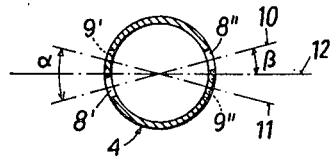

FIG. 4
FIG. 5
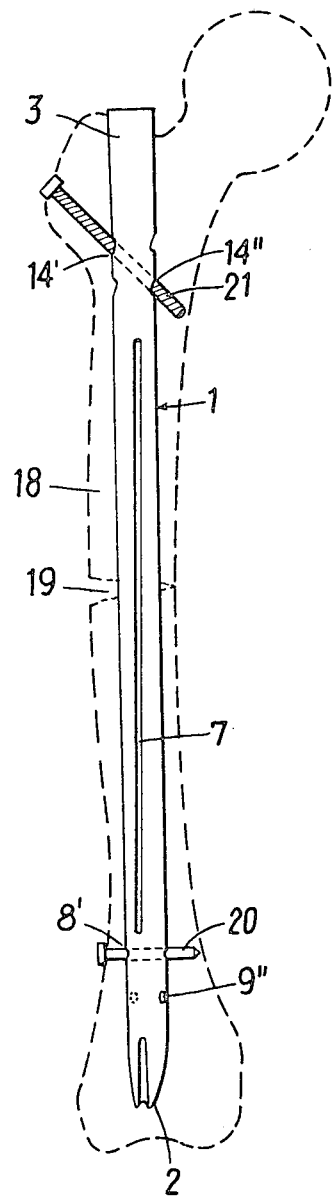
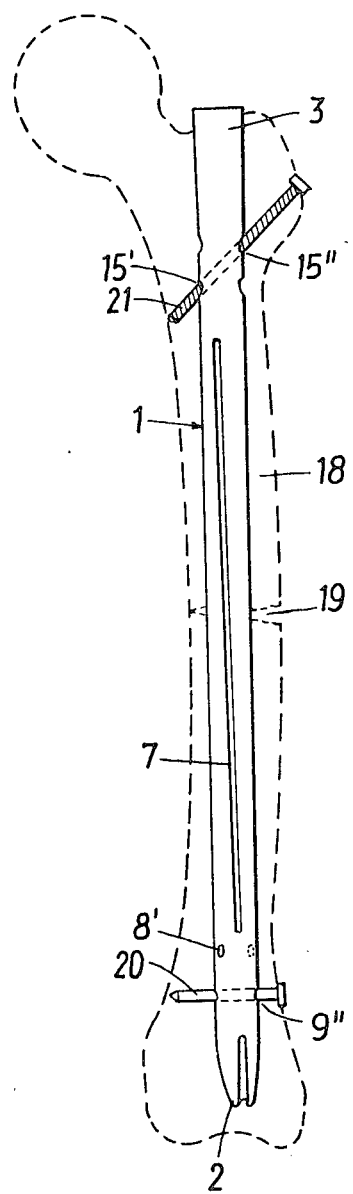

BONE-NAIL

The invention refers to a bone-nail for long hollow bones, in particular for femurs or thigh-bones and shanks or shin-bones.

BACKGROUND OF THE INVENTION

It is already known to care for fractures of femurs or thigh-bones by enlarging in diameter the marrow space by means of a boring fraise and subsequently driving a bone-nail into the marrow space having been enlarged in diameter. When nailing bones in usual manner, the diameter of the marrow space having been enlarged by fraising is greater for approximately 0.5 mm than the outer diameter of the bone-nail for the purpose of preventing jamming of the nail when driving same into the marrow space.

For effecting bone nailing with nails introduced into the marrow space, bone-nails have already been proposed, which consist of a straight tube having a cross section of the shape of a clover-leaf and being provided over the whole length with a longitudinal slot. It has further been proposed to slightly bend these nails for better adapting same to the curvature of the femur. It is also known to provide at the proximal end of the nails a head for applying a driving tool and having, for example, the shape of a cone provided with an internal thread. Known bone-nails have a tip at their distal end for facilitating insertion of the nails into the marrow space.

The longitudinal slot, which can be located either on the convex side or on the concave side of a bone-nail, allows a bone-nail made of a material showing a certain elasticity to reduce its diameter when being driven into the marrow space so that the bone-nail can engage the wall of the marrow space under tension.

It is also known to provide holes at the distal and at the proximal portions of bone-nails for marrow nailing and to insert bolts into these holes after having the nail driven into the marrow space, for anchoring the nail ends within the bone. Thus, the position of the nail is fixed on both sides of the fractured area and it is made sure that the bone does not become shortened after loading the bone immediately after the nailing operation, and this also in case of a fragmentation fracture. Insertion of the bolts is in this case effected by means of a sighting or aiming instrument determining the aligned position of the diametrically opposed holes and a guide means.

It is a drawback of known bone-nails that difficulties frequently arise when driving such nails into the widened marrow space in case the diameter of this marrow space corresponds to the nail diameter or is only slightly greater. When widening the marrow space by fraising, no smooth wall is formed but elevations result which represent an obstacle for sliding the bone-nail into the marrow space. Substantial difficulties can arise particularly if the distal and tipped edge portion of the nail becomes jammed during the driving operation. If, however, the marrow channel is widened by fraising to a diameter substantially exceeding the outer diameter of the nail, the bone is no more unobjectionally fixed in position at the location of fracture.

A further drawback of known bone nails must be seen in the fact that for nailing a right femur or thigh-bone not the same nail can be used as for nailing the left femur or thigh-bone. The reason therefor is that the bolt fixing the nail at the area of inserting this nail at the hip joint can for anatomic reasons not be arranged in normal direction to the longitudinal direction of the nail at this area but must be obliquely arranged, so that the position of the holes accommodating these mentioned bolts and located at the proximal edge portion of the nail is different with a nail for a right femur or thigh-bone and with a nail for a left femur or thigh-bone.

Finally, the known bone nails suffer from the disadvantage that application of the bolts within the area located distant from the hip becomes difficult on account of the nail becoming always rotated around its axis or twisted. For anatomic reasons, the axis of the bolt must, however, extend in normal direction to the plane comprising the curvature of the nail, the bolt being applied from the outside of the condyle of the femur or thigh-bone. In front of and behind this location there are bulky muscles through which the bolt can not be introduced and furthermore the upper knee-joint bag is located at the front side and extends relatively far in upward direction. If the nail becomes now twisted during driving operation on account of the shape of the femur or thigh-bone and in view of its elasticity, the holes originally arranged laterally with their axes substantially in normal position relative to the plane of curvature of the nails are located either in front of or behind that position at which the bolts must be arranged for anatomic reasons for not penetrating either the upper knee-joint bag or the bulky muscles.

It is an object of the present invention to avoid the drawbacks of the known bone-nails.

It is further an object of the invention that the nail can, on the one hand, be easily introduced by a driving operation and, on the other hand, reliably maintain the area of fracture in a fixed position. The nail shall easily find its path with its distal edge portion when being driven into the bone and shall smooth any roughness and any elevations within the marrow space but shall with its middle portion tightly and resiliently engage the wall of the marrow space for achieving a reliable fixation in position of the fractured area. It is a further object of the invention to provide a bone-nail which can be used for right-hand bones as well as for left-hand bones. It is also an object of the present invention to provide a bone-nail with which the driving force exerted on the head of the nail as well as any rotational force exerted on the head of the nail is uniformly distributed or transmitted onto the nail. It is a further object of the invention to design the bone-nail such that also in case of an unintended and undesired rotation of the nail during the driving operation a fixing bolt serving the purpose of anchoring the nail within the bone assumes a position normally extending relative to the plane of curvature of the nail, so that neither the knee-joint bag nor bulky muscles represent an obstacle for inserting the fixing bolt. Finally, it is an object of the invention to design the nail such that threaded bolts can be used as the fixing bolts at the proximal end portion.

BRIEF DESCRIPTION OF THE DRAWINGS

In the annexed drawings, the invention is schematically illustrated with reference to an embodiment.

FIG. 1 shows a side elevation of a bone-nail for a femur designed according to the invention and FIG. 2 shows a front elevation in direction of the arrow II in FIG. 1.

FIG. 3 shows a section along the line III—III in FIG. 2.

FIG. 4 shows a nail according to the invention as being inserted into a left femur or thigh-bone and FIG. 5 shows such a nail when being used in a right femur or thigh-bone, both bones being shown from the backside.

DETAILED DESCRIPTION OF THE DRAWINGS

The nail shown in the drawings and intended for the treatment of a fracture of the femur consists of a tubular base member 1 being provided at its distal end with a tip 2 and being proximally provided with a head 3 being adapted for being coupled with a driving instrument not shown. The head 3 had, for example, the shape of a tubular truncated cone being provided at its inner wall with a thread for screwedly engaging a correspondingly shaped driving instrument.

The base member 1 has a distal edge portion 4, a proximal edge portion 5 and a middle portion 6, located therebetween. Both edge portions 4,5 consist of a closed tube, i.e. a non-slotted tube, whereas the middle portion 6 is provided with a longitudinal slot 7 which is manufactured during the production of the nail by fraising operation effected on the closed tube. This longitudinal slot is being widened or enlarged to some extent for increasing the cross section of the nail in its middle portion 6 over the cross section in both edge portions 4,5.

If now the marrow space is subjected to boring operation such that its diameter exceeds the diameter of the closed tube for only 0.2 to 1.0 mm, the distal edge portion 4 adjoining the tip 2 easily finds its path into the marrow space and smoothens any unevenness if present, whereas the middle portion 6 having an increased cross section over the cross section of the edge portions 4,5 in view of having widened the longitudinal slot 7 snugly and resiliently contacts with pre-tension the wall of the marrow space and is thus unobjectionably fixing in position the area of fracture.

Two pairs 8', 8" and 9', 9" of holes are provided at the distal edge portion 4 and a bolt 20 (see FIGS. 4 and 5) can be passed therethrough for anchoring the nail in the bone. The holes 8', 8" of said one pair of holes are diametrally opposed and thus have a common axis 10 approximately being located in a plane normally extending relative to the longitudinal axis of the nail. Also the nails 9', 9" of said other pair of holes are diametrally opposed and thus have a common axis 11 being located within a normal plane approximately extending in parallel relation to the first-mentioned normal plane. Said both axes 10, 11 are not directed in parallel relation one relative to the other but are crossing one the other with an acute angle $\alpha$, which can, for example, assume a value between 10° and 60°.

The axes 10, 11 are further symmetrically arranged relative to the plane 12 extending in normal relation to the plane of curvature of the nail and include with this plane an angle $\beta$ which can assume a value between 5° and 30°. This embodiment provides the possibility to introduce the bolt 20 exactly laterally from the outer side of the condyle of the femur into one of said both pairs of holes which, on account of the nail having become twisted when being driven into the bone, now assumes a position in which the axis of the pair of holes extends approximately in normal direction relative to the plane of curvature of the nail in the distal edge portion, and this if the nail has become twisted during driving operation on account of the curvature of the femur or thigh-bone 18. Thus one can evade, when inserting the bolt 20, the bulky muscles located at the rear side and at the front side of the femur condyle and at the area of the knee and one can also evade the upper knee-joint bag. The degree of rotation or, respectively, torsion of the nail during driving same into the bone is dependent on the elasticity of the nail, i.e. dependent on the material used for manufacturing the nail. Nails of high elasticity are desired in principle because such nails snugly engage the wall of the marrow space under pre-tension with their middle portion being provided with the slot 7 and thus reliably fix in position the area of fracture which is shown at 19 in the FIGS. 4 and 5. Such nails of high elasticity become, however, twisted or rotated during driving operation to such an extent that the axes 10, 11 of the holes provided in these nails must be dislocated for a correspondingly great degree from the plane 12 extending in normal direction to the plane of curvature of the nail.

The position of the nail relative to the bone fragment is fixed by the bolts 20 introduced into the holes 8', 8" and, respectively, 9', 9" by means of a sighting instrument.

The tip 2 of the nail has an opening 13 comprising lateral wings through which a pike can pass which is arranged within the marrow space prior to driving the nail into the bone.

Two pairs 14', 14" and 15', 15" of holes are equally provided in the proximal edge portion 5, the holes 14', 14" having a common axis 16 and the holes 15', 15" having a common axis 17. As can be derived from FIG. 2, said axes 16, 17 are located in a common plane extending approximately normally relative to the plane 12 of curvature and intersect one another with an angle $\gamma$ which is approximately a right angle. Thus, the axes 16, 17 include with the longitudinal axis of the nail an angle of approximately 45°. This embodiment enables the inventive bone nail to be used for the left femur or thigh-bone shown in FIG. 4 as well as for a right femur or thigh bone shown in FIG. 5, the bolt 21 introduced into both holes of one of both pairs of holes assuming a position in which the bolt can easily be introduced with consideration of the anatomy and in which the bolt reliably secures the proximal edge portion 5 of the nail in position. The holes 14', 14", 15', 15" are conveniently provided with a thread so that screw bolts can be used as the bolts 21 for being screwed into the threaded holes. By means of these bolts 21, the position of the nail relative to the bone fragment is fixed at the proximal edge portion.

By fixing the nail within the bone 18 at the distal edge portion 4 as well as at the proximal edge portion 5, the bone is prevented from being shortened when being loaded before the healing process has started at the area 19 of fracture. This danger is present particularly with so-called fragmented fractures.

The slot 7 can be arranged at the concave side or at the convex side of the bent nail. With a nail intended for being used in the treatment of a femur fracture, the slot is preferably arranged at the concave side, which has the advantage that by slightly bending the femur and thus also the nail arranged within the marrow space of the femur, the diameter of the tube is expanded and an increase of stability in transverse direction is obtained.

A material suitable for a bone-nail according to the invention is, for example, steel or a steel alloy, if desired also titanium. The material and the wall thickness shall be coordinated such that te nail has the desired elasticity, i.e. effects spring movement on only small acting forces.

What is claimed is:

1. Bone-nail for long hollow bones, said nail consisting of a tubular base member distally provided with a tip and proximally comprising a head for applying a driving tool, the distal edge portion of the base member having a closed cross section, the middle portion adjoining the distal edge portion being slotted in longitudinal direction of the nail and the proximal edge portion adjoining this middle portion having a closed cross section and the slot being enlarged by forcibly bending its edges such that the middle portion has a cross section which is greater than the closed cross section of the edge portions, said distal edge portion having a closed cross section being provided with two pairs of holes, both holes of one pair of holes being coaxially arranged on a common axis extending through the nail in transverse direction relative to its longitudinal direction and said coaxial common axes of said both pairs of holes being located in different planes transversely extending relative to the longitudinal direction of the nail and crossing one another under an acute angle.

2. Bone-nail according to claim 1 wherein said both axes of the said both pairs of holes cross one another within the distal edge portion under an angle between 10° and 60°.

3. Bone-nail according to claim 1 wherein the nail axis extends along a curve and wherein said both axes of said both pairs of holes include within the distal edge portion an acute angle with a plane normally extending relative to the plane including the curved nail axis and extending in direction of the nail axis.

4. Bone-nail according to claim 1 wherein said both axes of the neighboured both pairs of holes within the distal edge portion include an angle between 5° and 30° with a plane normally extending relative to the plane including the curved nail axis and extending in direction of the nail axis.

5. Bone-nail according to claim 1 wherein the nail axis extends along a curve and wherein within said proximal edge portion having a closed cross section there are provided two pairs of holes, said both holes of one pair of holes being coaxially arranged on a common axis and said coaxial common axes of said both pairs of holes within the proximal edge portion having a closed cross section being located in a common plane substantially normally extending relative to the plane including the curved nail axis and extending in direction of the nail axis at the area of the said both pairs of holes, said both axes intersecting one another within the interior of the nail.

6. Bone-nail according to claim 5, wherein said both axes of said both pairs of holes within the proximal edge portion having a closed cross section include one with the other an angle of 90°.

7. Bone-nail according to claim 5 wherein the holes within the proximal edge portion having a closed cross section are provided with a thread.

* * * * *